(12) United States Patent
Riondel et al.

(10) Patent No.: US 9,296,679 B2
(45) Date of Patent: Mar. 29, 2016

(54) METHOD FOR THE PRODUCTION OF 2-OCTYL ACRYLATE BY MEANS OF TRANSESTERIFICATION

(71) Applicant: Arkema France, Colombes (FR)

(72) Inventors: Alain Riondel, Forbach (FR); Coralie Graire, Grezieu-la-Varenne (FR); Marc Esch, Freyming-Merlebach (FR)

(73) Assignee: Arkema France, Colombes (FR)

( * ) Notice: Subject to any disclaimer, the term of this patent is extended or adjusted under 35 U.S.C. 154(b) by 36 days.

(21) Appl. No.: 14/370,228

(22) PCT Filed: Jan. 14, 2013

(86) PCT No.: PCT/FR2013/050079
§ 371 (c)(1),
(2) Date: Jul. 2, 2014

(87) PCT Pub. No.: WO2013/110877
PCT Pub. Date: Aug. 1, 2013

(65) Prior Publication Data
US 2015/0203436 A1    Jul. 23, 2015

(30) Foreign Application Priority Data

Jan. 23, 2012 (FR) ...................................... 12 50606

(51) Int. Cl.
*C07C 67/03* (2006.01)
*C07C 67/54* (2006.01)

(52) U.S. Cl.
CPC ................. *C07C 67/03* (2013.01); *C07C 67/54* (2013.01); *B01J 2219/00006* (2013.01)

(58) Field of Classification Search
CPC .............................. C07C 67/03; C07C 67/54
See application file for complete search history.

(56) References Cited

U.S. PATENT DOCUMENTS 6,977,310 B2 * 12/2005 Ackermann et al. ..... C07C 67/03
560/217
7,268,251 B2    9/2007 Geisendoerfer et al.

FOREIGN PATENT DOCUMENTS

EP                960877              12/1999

OTHER PUBLICATIONS

Danni Liu et al, Rational Design of Pseudozyma Antarctica Lipase B Yielding a General Esterfication Catalyst, Chembiochem, vol. 11, No. 6, Apr. 12, 2010, pp. 789-795.

* cited by examiner

*Primary Examiner* — Yong Chu
(74) *Attorney, Agent, or Firm* — Lynn B. Morreale

(57) ABSTRACT

The invention relates to the production of 2-octyl acrylate of high purity and in good yield, that includes the recycling of economically upgradable products, such as un-reacted reactants and catalyst. The process uses ethyl titanate in solution in 2-octanol or 2-octyl titanate as a tranesterification catalyst and employs a purification train comprising only two distillation columns.

7 Claims, 1 Drawing Sheet

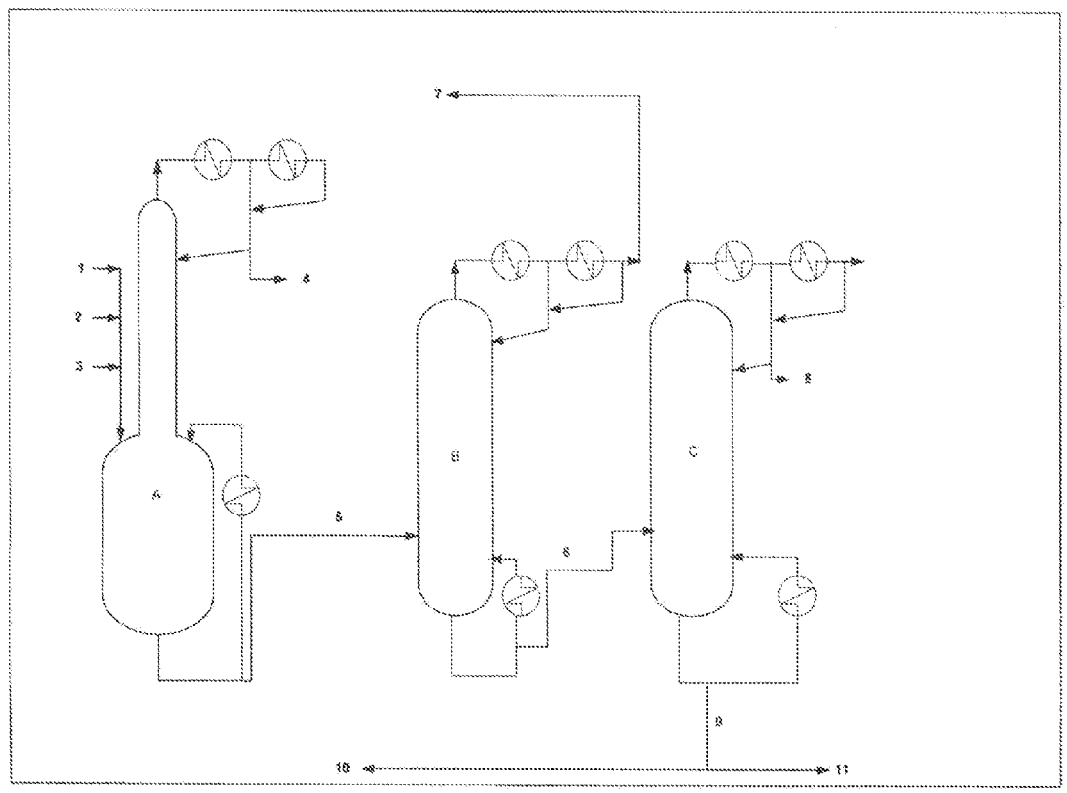

METHOD FOR THE PRODUCTION OF 2-OCTYL ACRYLATE BY MEANS OF TRANSESTERIFICATION

CROSS-REFERENCE TO RELATED APPLICATIONS

This application is a national stage application under 35 U.S.C. §371 of PCT/FR2013/050079, filed Jan. 14, 2013, which claims benefit to French patent application FR 1250606, filed Jan. 23, 2012.

FIELD OF THE INVENTION

The present invention relates to the production of 2-octyl acrylate according to a continuous process by transestertfication.

TECHNICAL BACKGROUND

It is known to produce acrylic esters by carrying out a transesterification reaction between an acrylate of a light alcohol (known as light acrylate) and a heavy alcohol.

This reaction is an equilibrated catalyzed reaction with generation of light alcohol, according to the formula (I):

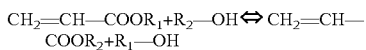

$$CH_2=CH-COOR_1+R_2-OH \Leftrightarrow CH_2=CH-COOR_2+R_1-OH$$

It is necessary to remove the light alcohol produced during the reaction in order to shift the equilibrium in the direction of the production of the acrylic ester.

This reaction is generally accompanied by side reactions which produce impurities which is necessary to remove for the purpose of obtaining the acrylic ester with a high purity satisfying the technical requirements related to its final use as monomer to manufacture polymers which can be used in numerous fields of application.

Furthermore, for obvious economic reasons, the economically upgradable products present in the crude reaction mixture, in particular the unreacted reactants and the catalyst, are, as far as possible, recycled within the process.

For these purposes, a separation/purification process comprising a combination of distillations, extractions and/or separations by settling is generally performed, which process is simultaneously relatively complex to carry out, in particular as a result of the presence of azeotropic mixtures, and expensive energetically.

Various transesterification processes for producing acrylic esters have already been described in the prior art.

Mention may be made, for example, of the document U.S. Pat. No. 7,268,251, in which the reaction effluent from the transesterification is treated in the following way:

either most of the desired acrylic ester is first of all separated and is subsequently isolated from the catalyst used by distillation (separation of catalyst), or it is first of all isolated from the catalyst used by distillation (separation of catalyst) and subsequently most of the acrylic ester is separated, and, subsequently, the compounds having a lower boiling point than that of the desired acrylic ester are separated by distillation of the mixture obtained (separation of low-boiling-point substances) and subsequently the acrylic ester is distilled (distillation in the pure state).

This process requires the use of at least four distillation or rectification columns, including an evaporator in order to separate the catalyst, generally a titanium alkoxide.

Even if the process described in the document U.S. Pat. No. 7,268,251 relates to the manufacture of alkyl acrylates by transesterification starting from an alkyl acrylate and from an alcohol exhibiting a chain length greater by at least one carbon with respect to the alkyl chain of the starting acrylate, this process is illustrated only with the manufacture of dimethylaminoethyl acrylate from dimethylaminoethanol and methyl acrylate or ethyl acrylate in a cascade of two reactors.

It turns out that the process described in the document U.S. Pat. No. 7,268,251 is complicated to carry out on the industrial scale, as a result of the optimization of the operating conditions of the succession of the four distillation/rectification components, in order to obtain a product of high purity and a satisfactory productive output.

The document U.S. Pat. No. 6,977,310 describes a process for the continuous manufacture of (meth)acrylic acid alkyl esters from methyl(meth)acrylate and from a $C_2$-$C_{12}$ alcohol in the presence of a tetraalkyl titanate as transesterification catalyst. This process consists in subjecting the reaction mixture to a distillation under reduced pressure which separates the easily volatile compounds (unreacted reactants) and then the resulting fraction exiting at the column bottom, comprising the ester produced, the catalyst, the polymerization inhibitors and the high-boiling-point byproducts, is sent to a vacuum distillation stage which makes it possible to recover, at the top, the ester produced of high purity. This vacuum distillation stage comprises in particular a film evaporator, combined with a distillation column, for complete removal of the high-boiling-point products in the ester produced.

This process is illustrated with the manufacture of butyl methacrylate and isobutyl methacrylate, respectively from butanol and isobutanol.

The process described in the document U.S. Pat. No. 6,977,310 employs a film evaporator to prevent any decomposition of the catalyst and any formation of ethers of the alcohol reactant. This process in addition does not provide for the recycling of the catalyst.

Surprisingly, it has been found that, in the case of 2-octyl acrylate, the removal of the catalyst using a conventional boiler and not a film evaporator does not result in the formation of impurities, such as ethers or octanes.

The applicant company, seeking to solve the various problems of the abovementioned processes, has thus discovered a simplified manufacturing process for producing 2-octyl acrylate of very high purity with a high yield, while including the recycling of the economically upgradable products, such as the unreacted reactants and the catalyst, and thus exhibiting a productive output compatible with manufacture on the industrial scale.

The solution provided consists in using ethyl titanate in solution in 2-octanol or 2-octyl titanate as transesterification catalyst and in employing a purification train comprising only two distillation columns.

The present invention makes it possible in addition to produce an acrylic ester comprising carbon of renewable origin related to the use of the 2-octanol, which is an alcohol derived from plant matter.

SUMMARY OF THE INVENTION

A subject matter of the present invention is a process for the continuous production of 2-octyl acrylate by a transesterification reaction between a light alcohol acrylate and 2-octanol in the presence of an alkyl titanate as transesterification catalyst and at least one polymerization inhibitor, the azeotropic mixture composed of light alcohol acrylate and of light alcohol generated by the transesterification reaction being withdrawn continuously during the reaction, the reaction mixture being subjected to a purification treatment comprising two distillation columns, in order to obtain, on the one hand, the pure 2-octyl acrylate and, on the other hand, the unreacted 2-octanol and light alcohol acrylate compounds intended to be recycled, and also the catalyst intended to be recycled, which process is characterized in that:

the catalyst is chosen from ethyl titanate in solution in 2-octanol and 2-octyl titanate;

the crude reaction mixture comprising the desired 2-octyl acrylate with, as light products, the unreacted 2-octanol and light alcohol acrylate and, as heavy products, the catalyst, the polymerization inhibitor or inhibitors and also heavy reaction products is sent to a first distillation column (B) under reduced pressure and a distillation is carried out, in said first column (B), which makes it possible to obtain:

at the top, a stream composed essentially of unreacted 2-octanol and light alcohol acrylate, with a minor fraction of 2-octyl acrylate, and at the bottom, a stream comprising 2-octyl acrylate, the catalyst, the polymerization inhibitor or inhibitors and the heavy reaction products and traces of light compounds; then the bottom stream from the first distillation column (B) is sent to a second distillation column (C) under reduced pressure, in which a distillation is carried out which makes it possible to obtain:

at the top, the desired pure 2-octyl acrylate; and at the bottom, the catalyst, the polymerization inhibitor or inhibitors and the heavy reaction products, and 2-octyl acrylate;

the bottom stream from the second distillation column (C) is recycled to the reaction, at least in part.

The invention is now described in more detail and without implied limitation in the description which follows, with reference to the single appended FIGURE, which diagrammatically represents a plant which makes it possible to implement the process according to the invention.

DETAILED DESCRIPTION

FIG. 1 is a schematic representation of a plant suitable to implement an embodiment of the inventive process.

One of the objectives of the invention is to use starting materials of natural and renewable origin, that is to say biosourced.

The 2-octanol used in the process according to the invention is an alcohol of renewable origin; in particular, it can be obtained by alkaline treatment of ricinoleic acid derived from castor oil.

The light alcohol acrylate employed as starting material in the process according to the invention is obtained by direct esterification of acrylic acid, essentially produced industrially from propylene, with a light alcohol, generally methanol or ethanol.

Independently of the use of 2-octanol of renewable origin, the invention extends to the use of a light alcohol acrylate derived from acrylic acid of renewable origin, which can in particular be obtained from glycerol, according to a process comprising a first stage of dehydration of the glycerol to give acrolein, followed by a stage of gas-phase oxidation of the acrolein thus obtained, or obtained by dehydration of 2-hydroxypropionic acid (lactic acid) or 3-hydroxypropionic acid and their esters.

The invention also extends to the use of a light alcohol acrylate derived from a biosourced alcohol, such as bioethanol.

Generally, the transesterification reaction is carried out in a stirred reactor (A), heated by an external exchanger and surmounted by a distillation column, with a light alcohol acrylate/2-octanol molar ratio which can range from 1 to 3, preferably between 1.3 and 1.8.

Use is made, as light alcohol acrylate, of methyl acrylate, ethyl acrylate or butyl acrylate, preferably ethyl acrylate.

The transesterification catalyst is ethyl titanate in solution in 2-octanol, for example a 90% solution of ethyl titanate in 2-octanol, or 2-octyl titanate, obtained beforehand by reaction of ethyl titanate with 2-octanol at 100° C., preferably 2-octyl titanate.

The catalyst is used in a proportion of $5 \times 10^{-4}$ to $5 \times 10^{-2}$ mol per mole of 2-octanol, preferably in a proportion of $10^{-3}$ to $10^{-2}$ mol per mole of 2-octanol.

The transesterification reaction is generally carried out in the reactor (A) at a pressure of between 500 mmHg ($0.67 \times 10^5$ Pa) and atmospheric pressure and at a temperature ranging from 90° C. to 130° C., preferably from 100° C. to 120° C.

The reaction is carried out in the presence of one or more polymerization inhibitors which are introduced into the reactor, in a proportion of 1000 to 5000 ppm with respect to the crude reaction mixture. Mention may be made, as polymerization inhibitors which can be used, for example, of phenothiazine, hydroquinone, hydroquinone monomethyl ether, di(tert-butyl)-para-cresol (BHT), TEMPO (2,2,6,6-tetramethyl-1-piperidinyloxy), di(tert-butyl)catechol or TEMPO derivatives, such as 4-hydroxy-TEMPO (4-OH-TEMPO), alone or their mixtures in all proportions. A further addition of polymerization inhibitor is generally carried out in the subsequent purification treatment, in particular in each of the distillation columns.

The light alcohol formed by the transesterification reaction is continuously entrained by distillation into the column surmounting the reactor in the form of an azeotropic mixture with the light alcohol acrylate. This mixture is advantageously recycled to the unit for the synthesis of the light acrylate.

After reaction with a residence time in the reactor generally of between 3 and 6 hours, the crude reaction mixture (5) comprises the desired 2-octyl acrylate with, as light products, the unreacted 2-octanol and light alcohol acrylate and, as heavy products, the catalyst, the polymerization inhibitor or inhibitors and also heavy reaction byproducts.

The reaction mixture is subjected to a purification treatment comprising two distillation columns (B) and (C), in order to obtain, on the one hand, the pure 2-octyl acrylate and, on the other hand, the unreacted 2-octanol and light alcohol acrylate compounds intended to be recycled, and also the catalyst intended to be recycled.

The first distillation column (B) generally operates under a pressure ranging from 20 to 50 mmHg ($0.027 \times 10^5$ Pa to $0.067 \times 10^5$ Pa) at a bottom temperature ranging from 120° C. to 150° C.

The top stream (7) from column (B) is mainly composed of the unreacted light products (light alcohol acrylate and 2-octanol), with a minor fraction of 2-octyl acrylate product. This stream (7) can advantageously be recycled to the transesterification reaction in the reactor (A).

The bottom stream (6) from column (B) is mainly composed of 2-octyl acrylate with the catalyst, the polymerization inhibitors and the heavy byproducts and can comprise residual traces of light compounds.

This stream (6) is subjected to a distillation in a second column (C) which generally operates under a pressure of 20 to 50 mmHg ($0.027 \times 10^5$ Pa to $0.067 \times 10^5$ Pa) and a temperature ranging from 120° C. to 150° C.

The column (C) makes it possible to recover, at the top (8), the purified 2-octyl acrylate.

At the bottom of the column (C), the catalyst, the heavy byproducts, the polymerization inhibitors and 2-octyl acrylate are separated in a stream (9).

A portion (10) of this stream (9) is advantageously recycled to the reaction in the reactor (A), the remainder (stream 11) being sent for destruction.

The pure 2-octyl acrylate (8) recovered at the top of the column (C) exhibits a purity of greater than 99.3%, indeed even of greater than or equal to 99.6%.

The following examples illustrate the present invention without, however, limiting the scope thereof.

Experimental Part

In the examples, the percentages are shown by weight, unless otherwise indicated, and the following abbreviations have been used:

EA: ethyl acrylate
2 OCTA: 2-octyl acrylate
PTZ: phenothiazine

Example 1

According to the Invention

A mixture comprising the ethyl acrylate and 2-octanol reactants, ethyl titanate as a 90% solution in 2-octanol as catalyst with PTZ as inhibitor, in the proportions by weight 53.8/45.6/0.6, is charged to a perfectly stirred reactor A heated by an external exchanger and surmounted by a packed distillation column having 12 theoretical plates.

The reactor is heated, while bubbling with air, and, as soon as the temperature reaches 115° C. under 500 mmHg ($0.67 \times 10^5$ Pa), EA (3) stabilized with 2500 ppm of PTZ, 2-octanol (1) and a mixture (2) of ethyl titanate in solution in 2-octanol (90% mixture), in proportions by weight 53.8/45.6/0.6, are continuously introduced.

At the column top, the EA/ethanol azeotrope (4), with a composition by weight of 35/55, is continuously withdrawn. This mixture (4) is recycled directly to the plant for manufacturing EA.

The crude reaction product (5) comprises the 2 OCTA formed, unreacted EA, unreacted 2-octanol and a mixture comprising the catalyst with the polymerization inhibitors and heavy derivatives, in proportions by weight 73/20, 1/6.3/0.6. The crude reaction product (5) is sent continuously to a first distillation column B having 15 theoretical plates which operates under reduced pressure and which is heated by an external exchanger. At the column B top, a mixture comprising 2500 ppm of PTZ in EA is introduced.

The column B separates, at the top, a mixture (7) comprising the unreacted reactants. EA and 2-octanol, with a minor fraction of 2 OCTA, with a composition by weight of 67/21/13, which is sent to the reaction stage.

At the bottom of the column B, a mixture (6) enriched in 2 OCTA and comprising the polymerization inhibitors, the catalyst and the heavy derivatives is recovered: this mixture has the composition by weight:

2 OCTA: 97.8%
EA: 100 ppm
2-octanol: 500 ppm
heavy derivatives+inhibitors+catalyst: 2.1%.

This mixture (6) is sent to a second distillation column C. At the top of column C, a mixture comprising 2500 ppm of HQME in 2 OCTA is introduced. The column C separates, at the top, the purified 2 OCTA (8) and, at the bottom, a stream (9) predominantly comprising the catalyst, the heavy derivatives, the polymerization inhibitors and 2-octyl acrylate. This stream (9) is largely (of the order of 90% by weight) recycled to the reactor A (stream 10), the remaining part (11) being sent for destruction.

The 2-octyl acrylate has the following purity:
2 OCTA: 99.5%
EA: 500 ppm
2-octanol: 1500 ppm Example 2

Comparative

The same synthesis as in example 1 was carried out but using, as catalyst, butyl titanate as replacement for ethyl titanate In this case, the stream (7) distilled at the top of the column B comprises, in addition to the unreacted reactants with a minor fraction of 2 OCTA, 15% of butyl acrylate originating from the reaction of the catalyst with the EA This stream (7), intended to be recycled to the reaction stage, required a preliminary purification by distillation on an additional column to remove the butyl acrylate, in order to limit the accumulation over time of butyl acrylate in the plant and the risk of contamination of the purified 2 OCTA Example 3

Comparative

The same synthesis as in example 1 was carried out but using, as catalyst, 2-ethylhexyl titanate as replacement for ethyl titanate.

In this case, 2 OCTA (9) with a purity of 97.3% was obtained at the top of the column C due to the presence of 2% of 2-ethylhexyl acrylate in the purified product.

The 2-octyl acrylate thus obtained does not offer the same performance in pressure-sensitive adhesives as a 2 OCTA having a purity of 99.5%.

The invention claimed is:

1. A process for the continuous production of 2-octyl acrylate by a transesterification reaction between a light alcohol acrylate and 2-octanol using an alkyl titanate as transesterification catalyst and at least one polymerization inhibitor, an azeotropic mixture comprising light alcohol acrylate and light alcohol generated by the transesterification reaction being withdrawn continuously during the reaction, a crude reaction mixture being subjected to a purification treatment comprising two distillation columns, in order to obtain, on the one hand, substantially pure 2-octyl acrylate and, on the other hand, unreacted 2-octanol and light alcohol acrylate compounds and also the catalyst all for recycle, wherein the process further comprises the steps of:

choosing the catalyst from the group consisting of ethyl titanate in solution in 2-octanol and 2-octyl titanate;

sending the crude reaction mixture comprising 2-octyl acrylate with, as light products, unreacted 2-octanol and light alcohol acrylate and, as heavy products, catalyst, polymerization inhibitor and also heavy reaction products to a first distillation column (B) having a top and a bottom and under reduced pressure for distillation in said first column (B), to obtain:

at the top, a top stream consisting essentially of unreacted 2-octanol, light alcohol acrylate, and a minor fraction of 2-octyl acrylate, and at the bottom, a bottom stream comprising 2-octyl acrylate, catalyst, polymerization inhibitor and heavy reaction products, and traces of light compounds; then sending the bottom stream from the first distillation column (B) to a second distillation column (C) having a top and bottom and under reduced pressure, for distillation to obtain:

at the top, substantially pure 2-octyl acrylate; and at the bottom, catalyst, the polymerization inhibitor and heavy reaction products, and 2-octyl acrylate;

recycling the bottom stream from the second distillation column (C) to the reaction, at least in part.

2. The process as claimed in claim 1, wherein the catalyst is 2-octyl titanate.

3. The process as claimed in claim 1 wherein the catalyst is used in a proportion of $5 \times 10^{-4}$ to $5 \times 10^{-2}$ mol per mole of 2-octanol.

4. The process as claimed in claim 1 wherein the reaction is carried out starting from ethyl acrylate.

5. The process as claimed in claim 1 wherein the light alcohol acrylate/2-octanol molar ratio ranges from 1 to 3.

6. The process as claimed in claim 1 wherein the transesterification reaction is carried out at a pressure of between 500 mmHg ($0.67 \times 10^5$ Pa) and atmospheric pressure ($10^5$ Pa) and at a temperature ranging from 90° C. to 130° C.

7. The process as claimed in claim 1 wherein the light alcohol acrylate is ethyl acrylate of renewable origin.

* * * * *